United States Patent [19]
Sherman et al.

[11] Patent Number: 5,797,911
[45] Date of Patent: Aug. 25, 1998

[54] MULTI-AXIAL BONE SCREW ASSEMBLY

[75] Inventors: Michael C. Sherman; Troy Drewry, both of Memphis, Tenn.

[73] Assignee: SDGI Holdings, Inc., Memphis, Tenn.

[21] Appl. No.: 719,161

[22] Filed: Sep. 24, 1996

[51] Int. Cl.$^6$ ................................................ A61B 17/70
[52] U.S. Cl. ........................................ 606/61; 606/73
[58] Field of Search ......................... 606/60, 61, 54, 606/57, 59, 72, 73; 623/17

[56] References Cited

U.S. PATENT DOCUMENTS

| | | | |
|---|---|---|---|
| 4,946,458 | 8/1990 | Harms et al. | 606/61 |
| 5,005,562 | 4/1991 | Cotrel | 606/61 |
| 5,176,680 | 1/1993 | Vignzud et al. | 606/61 |
| 5,207,676 | 5/1993 | Harms et al. | 606/61 |
| 5,207,678 | 5/1993 | Harms et al. | 606/61 |
| 5,217,497 | 6/1993 | Mehdian | 606/61 |
| 5,261,909 | 11/1993 | Sutterlin et al. | 606/61 |
| 5,261,912 | 11/1993 | Frigg | 606/61 |
| 5,360,431 | 11/1994 | Puno et al. | 606/61 |
| 5,443,467 | 8/1995 | Biedermann et al. | 606/65 |
| 5,466,237 | 11/1995 | Byrd, III et al. | 606/61 |
| 5,476,464 | 12/1995 | Metz-Stravenhagen et al. | 606/61 |
| 5,520,689 | 5/1996 | Schlapfer et al. | 606/61 |
| 5,520,690 | 5/1996 | Errico et al. | 606/61 |
| 5,531,746 | 7/1996 | Errico et al. | 606/61 |
| 5,549,608 | 8/1996 | Errico et al. | 606/61 |
| 5,554,157 | 9/1996 | Errico et al. | 606/61 |
| 5,569,247 | 10/1996 | Morrison | 606/61 |
| 5,575,792 | 11/1996 | Errico et al. | 606/61 |
| 5,578,033 | 11/1996 | Errico et al. | 606/61 |
| 5,584,833 | 12/1996 | Fournet-Fayard et al. | 606/61 |
| 5,584,834 | 12/1996 | Errico et al. | 606/61 |
| 5,586,984 | 12/1996 | Errico et al. | 606/61 |
| 5,607,426 | 3/1997 | Ralph et al. | 606/61 |
| 5,609,593 | 3/1997 | Errico et al. | 606/61 |
| 5,609,594 | 3/1997 | Errico et al. | 606/61 |

*Primary Examiner*—Guy V. Tucker
*Attorney, Agent, or Firm*—Woodard, Emhardt, Naughton, Moriarity & McNett

[57] ABSTRACT

A multi-axial bone screw assembly includes a bone screw having a partially spherical head. The bone screw head is truncated at an upper surface in which a tool receiving recess is defined. The assembly includes a receiver member including a central bore that defines a tapered recess to receive the head of the bone screw. The bore of the receiver member also defines a channel communicating with the recess and configured to receive a spinal rod therein. A portion of the channel is threaded to receive a set screw above the rod. The assembly also includes a crown member disposed between the rod and the head of the bone screw. As the set screw is tightened into the receiver member, the set screw compresses the rod against the crown member, which presses the head of the bone screw into the tapered recess. In one embodiment, the head of the bone screw includes a flared edge that penetrates at least the crown member as the assembly is tightened.

15 Claims, 2 Drawing Sheets

MULTI-AXIAL BONE SCREW ASSEMBLY

BACKGROUND OF THE INVENTION

The present invention concerns a bone screw assembly, particularly useful for engagement in the vertebrae of the spine. In particular, the invention contemplates a bone screw assembly that is capable of achieving multiple angular orientations with respect to an elongated rod extending along the spine.

Several techniques and systems have been developed for correcting and stabilizing the spine and for facilitating fusion at various levels of the spine. In one type of system, a bendable rod is disposed longitudinally along the length of the spine or vertebral column. The rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Another very prevalent fixation element is a spinal screw which can be threaded into various aspects of the vertebral bone.

In one typical procedure utilizing a bendable rod, the rod is situated on opposite sides of the spine or spinous processes. A plurality of bone screws are threaded into a portion of several vertebral bodies, very frequently into the pedicles of these vertebrae. The rods are affixed to these plurality of bone screws to apply corrective and stabilizing forces to the spine.

One example of a rod-type spinal fixation system is the TSRH® Spinal System sold by Danek Medical, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane that is parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allows the surgeon to easily engage a bent spinal rod to each of the fixation elements for final tightening.

Another rod-type fixation system is the Cotrel-Dubosset/ CD Spinal System sold by Sofamor Danek Group, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screws with this "open-back" configuration. Details of this technology can be found in U.S. Pat. No. 5,005,562 to Dr. Cotrel. One benefit of this feature of the CD® System is that the fixation element is positioned directly beneath the elongated rod. This helps reduce the overall bulkiness of the implant construct and minimizes the trauma to surrounding tissue.

On the other hand, these fixation elements of the CD® System are capable only of pivoting about the spinal rod to achieve variable angular positions relative to the rod. While this limited range of relative angular positioning is acceptable for many spinal pathologies, many other cases require more creative orientation of a bone screw, for instance, relative to a spinal rod. Certain aspects of this problem are addressed by the variable angle screw of the TSRH® System, as discussed in the '909 Patent. However, there is a need for a bone screw that is capable of angular orientation in multiple planes relative to the spinal rod. Preferably, the bone screw is capable of various three-dimensional orientations with respect to the spinal rod. Screws of this type have been referred to as poly-axial or multi-axial bone screws.

Others have approached the solution to this problem with various poly-axial screw designs. For example, in U.S. Pat. No. 5,466,237 to Byrd et al., a bone screw is described which includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

In another approach shown in U.S. Pat. No. 4,946,458: to Harms et al., a spherical headed, bone screw is supported within separate halves of a receiver member. The bottom of the halves are held together by a retaining ring. The top of the receiver halves are compressed about the bone screw by huts threaded onto a threaded spinal rod. In another approach taken by Hanns et al., in U.S. Pat. No. 5,207,678, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts. It is known that threaded rods can tend to weaken the rods in the face of severe spinal loads. Moreover, the design of the bone screws in the '458 and '678 Patents require a multiplicity of parts and are fairly complicated to achieve complete fixation of the bone screw.

There is therefore a need remaining in the industry for a multi-axial or poly-axial bone screw that can be readily and securely engaged to an elongated spinal rod. Preferably, the spinal rod can be of any configuration—i.e., smooth, roughened, knurled or even threaded. This need also encompasses the need for minimizing the profile and bulk of any of the components used to engage the bone screw to the spinal rod in a variety of angular orientations.

SUMMARY THE INVENTION

In one embodiment of the invention, a spinal fixation assembly is provided that includes a bone engaging fastener, or bone screw, and an elongated member, such as a spinal rod. The fixation assembly includeds a multi-axial assembly that permits fixation of the bone screw to the spinal rod at any of a plurality of angles in three-dimensional space relative to the rod. In one aspect of the invention, the bone screw includes a head that is partially spherical. The head is preferably truncated to form a flat upper surface within which a tool engaging recess is defined.

The multi-axial assembly further includes a receiver member defining a bore therethrough from a top end to a bottom end. The bore includes a recess for receiving the head of the bone screw, with a lower opening at the bottom end of the receiver member through which the lower portion of the bone screw extends. The receiver member also includes a channel communicating with the recess and having an upper opening at the top end of the receiver member for insertion of the spinal rod.

In a further aspect of the invention, the assembly includes a crown member insertable through the upper opening of the receiver member and slidably disposed within the bore. The crown member has a lower surface contacting the head of the bone screw and an opposite upper surfaces contacting the spinal rod. In one embodiment, the crown member defines a bore which forms a conical bore at the lower surface contacting the head of the bone screw.

The assembly includes a compression member, such as a set screw, engaged within the bore at the upper opening of the receiver member. The compression member is operable to press the rod against the crown member, which then presses the head of the bone screw into the receiver member recess to thereby fix the head and bone screw at a particular angular orientation relative to the spinal rod.

In a further feature of the invention, the head of the bone screw includes a flared edge at the truncated upper surface. The flared edge is configured to penetrate the conical bore of the crown member to form a firm engagement between the two components. The flared edge can also be arranged to penetrate the recess of the receiver member at certain angular orientations of the bone screw head.

The present invention provides an assembly that fixes a bone engaging fastener to an elongated member at a plurality of angular orientations relative to the elongated member. The preferred embodiment of a multi-axial bone screw assembly provides the advantage of a solid fixation between a spinal rod and a bone screw, regardless of the angle between the two components.

A further benefit of the present invention resides in the minimum number of components necessary to effect this solid fixation. Another benefit is realized by the flared edge of the bone screw that enhances the fixation between the components. Other benefits and certain objects of the invention will become apparent upon consideration of the following written description and accompanying figures illustrating one embodiment of the invention.

DESCRIPTION OF THE PREFERRED EMBODIMENT

Figures 1, 2:
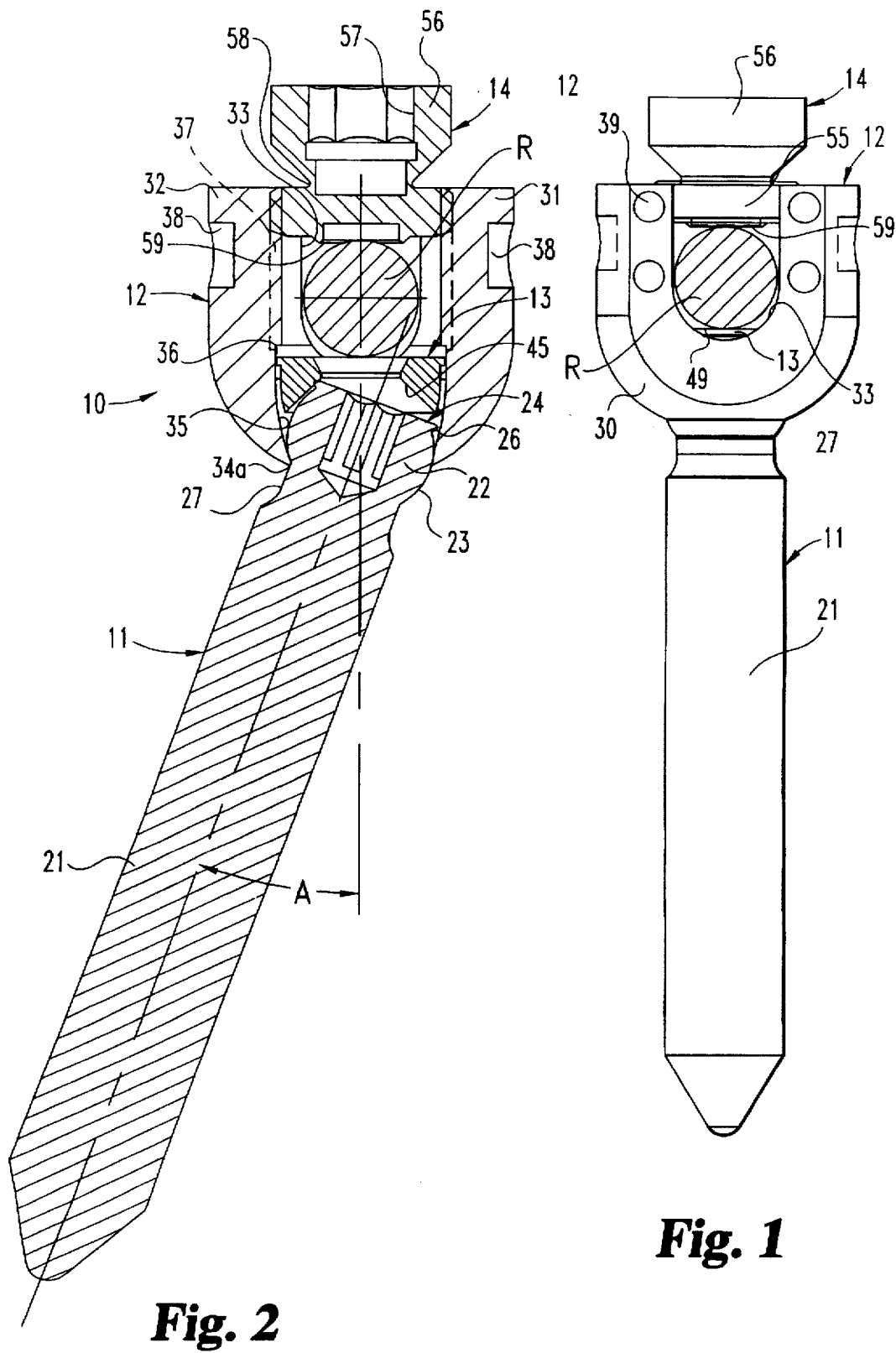
FIG. 1 is a side elevational view of a multi-axial bone screw assembly in accordance with one embodiment of the present invention, shown engaged to an elongated spinal rod.
FIG. 2 is a cross-sectional view of a multi-axial bone screw assembly as depicted in FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1 and 2, the general components of a multi-axial bone screw assembly 10 in accordance with the present invention are shown. The multi-axial bone screw assembly 10 includes a bone, screw 11 configured to engage a bone, such as a vertebra. The assembly further includes a receiver member 12 for supporting the bone screw, a crown member 13 for engagement with the bone screw, and a compression member 14 that is disposed within the receiver member 12 to clamp a spinal rod R within the assembly 10.

Figure 3:
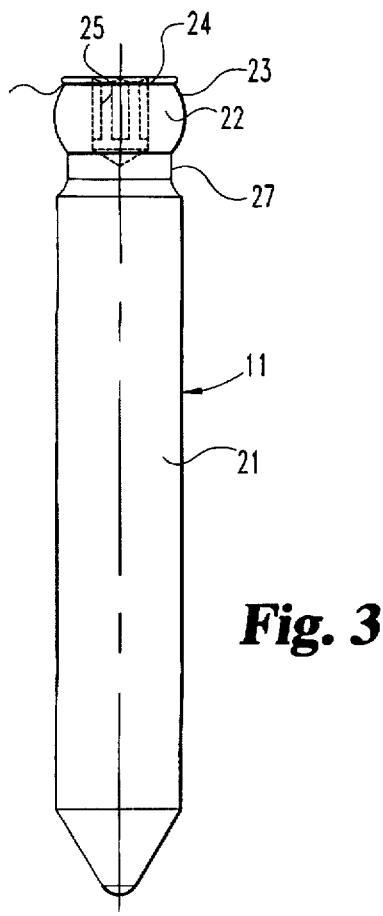
FIG. 3 is a side elevational view of a bone screw for use in the bone screw assembly shown in FIGS. 1 and 2.

In accordance-with one aspect of the invention, the bone screw 11 is configured as shown in FIG. 3. In particular, the bone screw 11 includes a threaded shank 21 that preferably carries threads configured to solidly anchor the bone screw within a bone. Most preferably, the threads are cancellous threads, or threads readily adapted for solid fixation within the cancellous bone of the vertebral body. It is understood that the threaded shank 21 can have a variety of configurations depending upon the nature of the bone within which the bone screw 11 is engaged. Moreover, the length of the threaded shank 21 can be adjusted depending upon the bone within which the screw is driven. In one specific embodiment, the threaded shank 21 has a length of about 1.75 inches, and is configured with threads for engagement within the pedicle of a lumbar vertebra.

The bone screw 11 further includes a head 22 at its upper or proximal portion. The head 22 defines a partially spherical outer surface 23. It has been found that a spherical surface is optimum in providing multi-axial angular variations of the position of the bone screw 11 relative to a spinal rod R. In one specific embodiment, the head 22, and specifically the spherical surface 23, resides at a diameter of 0.315 inches. As shown in FIG. 3, the head 22 does not form a complete sphere, having been truncated at an upper surface 24. Again, in a specific embodiment, the head 22 has a height of 0.196 inches as measured between the truncated upper surface 24 and the lower truncation of the head at the transition shank 27.

The head 22 defines a tool receiving recess 25 projecting into the head from the upper surface 24. In one embodiment, the recess 25 is a hex recess to receive a hex end driving tool as is known in the art. It is of course understood that the tool receiving recess 25 can have various configurations, such as a TORX® configuration.

As mentioned above, the head 22 is engaged to the threaded shank 21 of the bone screw 11 by way of a transition shank 27. As shown in FIG. 3 in accordance with the preferred embodiment, the transition shank 27 has a diameter that is less than the diameter of the head 22. As shown in FIG. 2, the reduced diameter transitional shank 27 provides clearance for the bone screw when it is oriented, at its greatest angle relative to the receiver member 12. In one specific embodiment, the transition shank 27 has a diameter of 0.236 inches, which is about 0.08 inches smaller than the diameter of the head 22.

Figure 4:
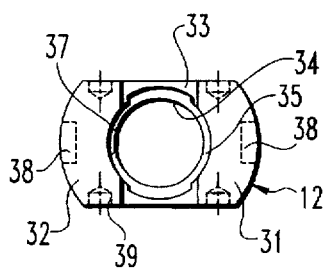
FIG. 4 is a top elevational view of a receiver member used to support the bone screw of FIG. 3 in the multi-axial bone screw assembly of FIGS. 1 and 2.
Figure 5:
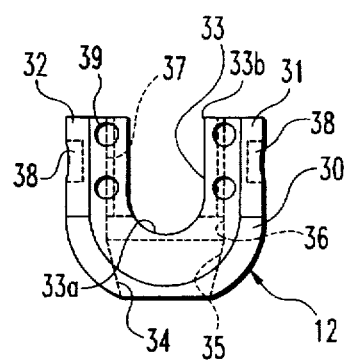
FIG. 5 is a side elevational view of the receiver member shown in FIG. 4.

Referring again to FIG. 2, a receiver member 12 is provided to support both the bone screw head 22 and the spinal rod R. The details of the receiver member 12 can also be seen with reference to FIGS. 4 and 5. In one aspect of the invention, the receiver member 12 includes a U-shaped body 30 defining a first branch 31 and a second branch 32. The branches form a channel 33 between each other. The channel terminates in an edge 33a on opposite sides of the U-shaped body 30. Preferably, the channel 33 has a width that is slightly larger than the diameter of a spinal rod to which the bone screw 11 is to be engaged. The channel 33 has an opening 33b at the top of the member 12 for insertion of the rod R, bone screw 11 and collet 13.

The receiver member 12 further defines a central bore 34 through the body 30. The lowermost portion of the bore 34 defines a tapered recess 35 within which the head 22 of the bone screw 11 resides, as shown in FIG. 2. The central bore also includes a crown recess 36 that is directly above the tapered recess 35. The crown recess opens into a threaded portion 37 which extends to the top opening 33b of the channel 33. The receiver member 12 is preferably sized for minimal bulk and minimum prominence above the spine. In one specific embodiment, the receiver member has a height of about 0.597 inches. In this specific embodiment, a rod disposed within channel 33 can sit as low as 0.2 inches above the surface of the vertebra when the receiver member 12 contacts the bone.

In one aspect of the receiver member 12, opposite tool recesses 38 are provided in each of the branches 31 and 32. The tool recesses are configured to be engaged by an insertion tool, such as an insertion tool used to insert spinal hooks into the spine. The receiver member 12 can also define a number of gripping holes 39 at the laterally adjacent sides of the body. In the specific illustrated embodiment, four such holes are provided on both sides of the receiver member 12. These gripping holes can be engaged by an appropriately configured gripping tool to support the receiver member 12 during tightening of the bone screw and the other components of the bone screw assembly 10.

In the preferred embodiment, the central bore 34 exits the U-shaped body 30 at a bottom opening 34a. The bottom opening 34a has a diameter that is smaller than the diameter of the head of the bone screw. Consequently, the bone screw is inserted through the upper opening 33b of the channel 33 and through the central bore 34 until it contacts the lower opening 34a of the bore 34. In one specific embodiment, the lower opening 34a has a diameter of 0.297 inches which is about 0.02 inches smaller than the diameter of the bone screw head 22. The tapered-recess 35 then expands from this diameter of the lower bore 34a to a larger diameter adjacent the crown recess 36. In one specific embodiment, this larger diameter is 0.370 inches, which is larger than the outer diameter of the head 22 of the bone screw 11. In this specific embodiment, the tapered recess 35 is tapered at an angle of about 11° from the lower opening 34a to the crown recess 36. Again, in the specific embodiment, this tapered recess has a height between the two ends of the recess of about 0.188 inches. The tapered recess 35 can assume various orientations and angles, depending upon the range of angles desired for the bone screw 11 to achieve relative to the spinal rod. As shown in FIG. 2, the bone screw 11 can be oriented at an angle A relative to a plane extending through the center of the spinal rod R. The range of this angle A can be determined by the diameter of the transition shank 27 of the bone screw 11 as well as the angle of the tapered recess 35. In the specific illustrated embodiment, the bone screw is capable of achieving a range of angles A up to 20°.

The threaded portion 37 of the U-shaped body 30 is configured to engage the compression member 14, which is preferably a set screw. In particular, referring to FIG. 2, the set screw 14 includes a threaded plug 55 having threads configured to engage the threaded portion 37 of the receiver member 12. The set screw 14 also includes a driving head 56 that defines a tool recess 57. In this specific embodiment, the tool recess can be a hex recess. Alternatively, the driving head 56 itself can have an external configuration to receive a driving tool. In accordance with the preferred embodiment, the set screw 14 is a "break-off type" set screw in which the driving head 56 is severed from the threaded plug 55 at ad shear zone 58. As is known in the art, the head of the break-off set screw will severe at a pre-determined torque, the torque being based upon the resistance offered by the head 22 of the bone screw, crown member 13 and the spinal rod R as they are compressed together between the receiver member 12 and the set screw 14.

Figure 6:
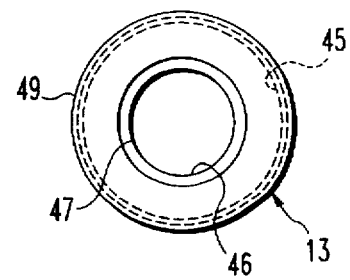
FIG. 6 is a top elevational view of a crown member for engagement between the bone screw of FIG. 3 and a spinal rod, in connection with the multi-axial bone screw assembly shown in FIGS. 1 and 2.
Figure 7:
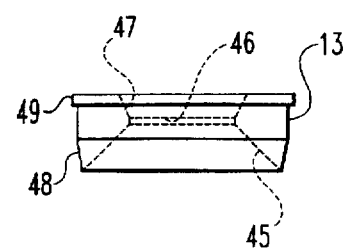
FIG. 7 is a side elevational view of the crown member shown in FIG. 6.

In a further aspect of the invention, the bone screw assembly 10 includes a crown member 13. The details of the crown member are shown in FIGS. 6 and 7. In particular, the crown member 13 is hollow and defines a conical bore 45 at its lower end. As shown in FIG. 2, the head 22 of the bone, screw 11 at least partially resides within the conical bore 45 of the crown member when the screw assembly 10 is affixed together. The crown member 13 further defines a tool insertion bore 46 that can be oriented directly over the tool receiving recess 25 of the bone screw 11 when the bone screw is situated within the receiver member 12. Crown member 13 also defines a conical tool relief 47 at the top of the tool insertion bore 46. This relief is oriented at an angle to permit positioning of a driving tool into the head of the bone screw 11 even when the receiver member 12 is not directly aligned with the bone screw.

Crown member 13 also forms a conical outer surface 48 that is preferably complementary with the tapered recess 35 of the receiver member 12. The member 13 also includes a rim 49 at its upper end. In accordance with one aspect of the invention, the rim 49 of the crown member 13 has a diameter that is slightly smaller than the diameter of the crown recess 36. The diameter of the collet recess 36, and also the rim 49 of the crown member 13, is slightly larger than the inner diameter of the threaded portion 37 of the receiver member 12. In this manner, the crown member 13 can be retained within the crown recess 36 when the multi-axial bone screw assembly 10 is only loosely connected. In accordance with the preferred embodiment of the invention, the rim 49 can be threaded through the threaded portion 37 of the receiver member 12 from the upper opening 33b of the channel 33 until it is disposed within the crown recess 36. The rim 49 can also be provided with a single thread to mate with the internal threads of the threaded portion 37, to facilitate insertion of the crown member 13 into the receiver member 12.

In one specific embodiment, the crown member has an outer diameter of 0.358 inches at the rim 49. This diameter is about 0.012 inches larger than the inner diameter of the threaded portion 37, and is about 0.012 inches smaller than the diameter of the crown recess 36. The conical bore 45 is preferably oriented at an angle of about 45°, so that at its open end the conical bore 45 has a diameter of about 0.324 inches, which is larger than the diameter of the head 22 of the bone screw 11.

When the multi-axial bone screw assembly 10 is to be used, the bone screw 11 is inserted into a receiver member 12 so that the screw extends through the bottom opening 34a of the central bore 34. At this point, the receiver member 12 can be supported at the tool recesses 38 by a gripping tool. The tool recess 38 of the bone screw 11 can be engaged by a driving instrument to thread the bone screw 11 into the vertebral bone. Once the bone screw 11 has been driven into its predetermined depth into the bone, the crown member 13 can be placed within the receiver member 12 and oriented on top of the head 22 of the bone screw 11. The receiver member 12 can then be engaged by way of the gripping holes 39 by a gripping tool to support the receiver member as the various components of the assembly 10 are tightened against each other. The spinal rod R can be pushed into the upper opening 33b of the channel 33 and into the channel 33. Once the spinal rod R is brought to bear against the crown member 13, the member should assume its final orientation relative to the head 22 of the bone screw 11. As shown in FIG. 2, in this orientation, the flared edge 26 of the head 22 of the bone screw 11 contacts the conical bore 45 of the crown member 13 somewhere above the bottom of the crown member and adjacent the tool insertion bore 46. At this orientation, the flared edge 26 also contacts the tapered recess 35 of the receiver member 12.

With the spinal rod R in position, the set screw 14 can be threaded into the threaded portion 37 of the receiver member 12. As the set screw 14 is tightened further into the receiver member 12, the tapered recess 35 of the receiver member 12 and the set screw 14 are drawn toward each other. As this process continues, the spinal rod R presses against the top of the crown member 13, which then presses against the head 22 of the bone screw 11. As the compression continues, the flared edge 26 of the bone screw 22 penetrates or bites into the conical bore 45 of the crown member 13. The flared edge 26 also preferably penetrates the tapered recess 35 of the receiver member 12. The penetration of the flared edge 26 helps prevent disengagement between the crown member, receiver and bones crew head under severe spinal loads, thereby adding a great degree of security of the fixation of the bone screw 11 to the spinal rod R.

As the set screw 13 is tightened further into the threaded portion 37 of the receiver member, the bone screw head 22 resists further movement into the tapered recess 35. Further tightening of the set screw requires greater torque until the screw head 56 is severed from the threaded plug 55 at the shear zone 58. Preferably, the shear zone is disposed within the receiver member 12 so that no portion of the set screw 14 projects beyond the opening 33b of the receiver member.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, the specific embodiment of the multi-axial bone screw assembly 10 can be sized for placement at any level of the spine. Of course, it is understood that the relative size of the components of the assembly will be modified for the particular vertebral to be instrumented. Likewise, the relative dimensions of the bone screw and receiver member can be modified to permit greater or lesser degrees of angulation of the bone screw relative to the spinal rod.

In the preferred embodiment, the components of the assembly 10 are formed of stainless steel. It is contemplated that the assembly 10 can be formed of other biocompatible materials, such as titanium, and even materials that permit bone ingrowth.

Further, while the preferred embodiment of the invention concerns a bone screw, other bone fixation members can be adapted to implement the multi-axial capabilities of this invention. For instance, a vertebral hook can be equipped with a spherical head to be clamped to a spinal rod by way of the components of assembly 10.

It is also understood that while the preferred embodiment of the invention engages a bone screw to a rod, various longitudinal members are contemplated. For example, an elongated bar can be disposed within the channel of the receiver member to be clamped between the crown member and set screw. The present invention can be applied equally well to smooth rods or bars, or longitudinal members having various surface features, such as knurling or threading.

What is claimed is:

1. A spinal fixation assembly, comprising:
   an elongated member configured for placement adjacent and along the length of the spine;
   a bone engaging fastener, said fastener having a lower portion configured for engaging a vertebra and an enlarged head;
   a receiver member defining a bore therethrough from a top end to a bottom end, said bore including a recess for receiving said head of said bone engaging fastener therein, said recess having a lower opening at said bottom end of said receiver member through which said lower portion of said fastener extends, said member also including a channel communicating with said recess and having an upper opening at said top end of said receiver member, said channel being configured to receive said elongated member therein adjacent said recess;
   a crown member insertable through said upper opening and slidably disposed within said recess, said crown member having a lower surface contacting said head of said fastener and an opposite upper surface contacting said elongated member, said head including a surface configuration for relative penetration into said lower surface; and
   a compression member engaged within said bore adjacent said upper opening, said compression member operable to press said elongated member against said crown member and said crown member against said head of said fastener for relative penetration therebetween, to thereby fix said head of said fastener between said crown member and said recess of said receiver member.

2. The spinal fixation assembly according to claim 1, wherein:
   said bore includes an internally threaded portion adjacent said upper opening; and
   said compression member is a set screw having threads for engagement with said internally threaded portion.

3. The spinal fixation assembly according to claim 1, wherein said head of said bone engaging fastener includes a truncated upper surface, and defines a tool receiving recess through said upper surface.

4. The spinal fixation assembly according to claim 1, wherein said head of said bone engaging fastener includes a truncated upper surface and a flared edge adjacent said upper surface, said flared edge arranged to penetrate at least said lower surface of said crown member when said head of said fastener is fixed between said crown member and said recess.

5. The spinal fixation assembly according to claim 1, wherein said lower surface of said crown member is a conical surface.

6. The spinal fixation assembly according to claim 1, wherein said crown member defines a bore therethrough, said bore including said lower surface contacting said head of said fastener, and said bore including a tool insertion bore configured to receive a driving tool to engage said head of said fastener through said bore of said crown member.

7. The spinal fixation assembly according to claim 1, wherein:
    said bore of said receiver member includes a portion for engaging said compression member and a crown recess between said portion and said recess, said portion having an inner diameter smaller than an inner diameter of said crown recess; and
    said crown recess includes an upper rim having a diameter smaller than the inner diameter of said crown recess but larger than the inner diameter of said portion of said bore.

8. The spinal fixation assembly according to claim 1, wherein said recess is conically tapered from a larger diameter to a smaller diameter at said bottom end.

9. The spinal fixation assembly according to claim 8, wherein said crown member includes a conical outer surface configured for complementary engagement with said tapered recess of said receiver member.

10. A spinal fixation assembly, comprising:
    an elongated member configured for placement adjacent and along the length of the spine;
    a bone engaging fastener, said fastener having a lower portion configured for engaging a vertebra and an enlarged head;
    a receiver member defining a bore therethrough from a top end to a bottom end, said bore including a recess for receiving said head of said bone engaging fastener therein, said recess having a lower opening at said bottom end of said receiver member through which said lower portion of said fastener extends, said bore further including an upper portion and a crown recess between said upper portion and said recess,
    said receiver member also including a channel communicating with said recess and having an upper opening at said top end of said receiver member, said channel being configured to receive said elongated member therein adjacent said recess;
    a crown member insertable through said upper opening and slidably disposed within said recess, said crown member having a lower surface contacting said head of said fastener and an opposite upper surface contacting said elongated member;
    means cooperating between said crown member and said said upper portion of said bore of said receiver member to prevent removal of said crown member from said crown recess when said crown member is slidably disposed therein prior to reception of the elongated member in the channel; and
    a compression member engaged within said upper portion of said bore, said compression member operable to press said elongated member against said crown member, to thereby fix said head of said fastener between said crown member and said recess of said receiver member.

11. The spinal fixation assembly according to claim 10, wherein said means to prevent removal includes:
    said crown recess having an inner diameter greater than an inner diameter of said upper portion; and
    said crown member including an upper rim at said upper surface having a diameter smaller than said inner diameter of said crown recess but larger than said inner diameter of said upper portion of said bore.

12. The spinal fixation assembly according to claim 11, wherein:
    said upper portion of said bore includes internal threads;
    said compression member is a set screw having threads for engagement with said internal threads; and
    said upper rim of said crown member is configured to be threaded between said internal threads, whereby said crown member is threadedly advanced through said upper portion into said crown recess.

13. The spinal fixation assembly according to claim 12, wherein said upper rim of said crown member includes at least one thread for mating with said internal threads.

14. A spinal fixation assembly, comprising:
    an elongated member configured for placement adjacent and along the length of the spine;
    a bone engaging fastener, said fastener having a lower portion configured for engaging a vertebra and a head, said head being at least partially spherical in configuration;
    a receiver member defining a bore therethrough from a top end to a bottom end, said bore including a recess for receiving said head of said bone engaging fastener therein, said recess having a lower opening at said bottom end of said receiver member through which said lower portion of said fastener extends, said member also including a channel communicating with said recess and having an upper opening at said top end of said receiver member, said channel being configured to receive said elongated member therein adjacent said recess,
    said head including a surface configuration for relative penetration into said recess of said receiver member;
    a crown member insertable through said upper opening and slidably disposed within said recess, said crown member having a lower surface contacting said head of said fastener and an opposite upper surface contacting said elongated member; and
    a compression member engaged within said bore adjacent said upper opening, said compression member operable to press said elongated member against said crown member, said crown member against said head of said fastener and said head against said recess, to thereby fix said head of said fastener between said crown member and said recess of said receiver member with relative penetration between said receiver member and said head of said fastener.

15. A spinal fixation assembly, comprising:
    an elongated member configured for placement adjacent and along the length of the spine;
    a bone engaging fastener, said fastener having a lower portion configured for engaging a vertebra and a head, said head being at least partially spherical in configuration and having a spherical diameter;
    a receiver member defining a bore therethrough from a top end to a bottom end, said bore including a recess for receiving said head of said bone engaging fastener therein, said recess having a lower opening at said bottom end of said receiver member through which said lower portion of said fastener extends, said member also including a channel communicating with said recess and having an upper opening at said top end of said receiver member, said channel being configured to receive said elongated member therein adjacent said recess, said recess being tapered from a diameter larger than said spherical diameter of said head of said fastener to a diameter at said lower opening smaller than said spherical diameter, said recess of said receiver member and said head configured for relative penetration between each other;

a crown member insertable through said upper opening and slidably disposed within said recess, said crown member having a conical lower surface contacting said head of said fastener and an opposite upper surface contacting said elongated member, said head of said fastener including a surface configuration for relative penetration into said lower surface of said crown member; and a compression member engaged within said bore adjacent said upper opening, said compression member operable to press said elongated member against said crown member, said crown member against said head of said fastener and said head against said recess, to thereby fix said head of said fastener between said crown member and said recess of said receiver member with relative penetration between said head of said fastener and both said recess and said conical lower surface of said crown member.

* * * * *